(12) United States Patent
Kunita

(10) Patent No.: US 8,100,832 B2
(45) Date of Patent: Jan. 24, 2012

(54) ULTRASOUND DIAGNOSTIC APPARATUS

(75) Inventor: Masanori Kunita, Mitaka (JP)

(73) Assignee: Hitachi Aloka Medical, Ltd., Mitaka-shi, Tokyo (JP)

( * ) Notice: Subject to any disclaimer, the term of this patent is extended or adjusted under 35 U.S.C. 154(b) by 283 days.

(21) Appl. No.: 12/107,461

(22) Filed: Apr. 22, 2008

(65) Prior Publication Data

US 2008/0269612 A1    Oct. 30, 2008

(30) Foreign Application Priority Data

Apr. 27, 2007  (JP) ................................ 2007-118366
Jan. 23, 2008  (JP) ................................ 2008-12280

(51) Int. Cl.
*A61B 8/14* (2006.01)
*A61B 8/00* (2006.01)

(52) U.S. Cl. ........................ 600/457; 600/453
(58) Field of Classification Search ............... 600/437
See application file for complete search history.

(56) References Cited

U.S. PATENT DOCUMENTS

| | | | |
|---|---|---|---|
| 4,167,879 A | 9/1979 | Pedersen | |
| 4,176,351 A | 11/1979 | DeVita et al. | |
| 4,578,677 A | 3/1986 | Lewis | |
| 5,022,400 A | 6/1991 | Walters | |
| 5,224,482 A | 7/1993 | Nikoonahad et al. | |
| 6,179,781 B1 | 1/2001 | Phillips | |
| 6,918,875 B2 | 7/2005 | Moriya et al. | |
| 6,953,434 B2 | 10/2005 | Hao et al. | |
| 6,960,169 B2 | 11/2005 | Mao et al. | |
| 7,094,204 B2 | 8/2006 | Banjanin et al. | |
| 7,338,450 B2 | 3/2008 | Kristoffersen et al. | |
| 7,698,948 B2 | 4/2010 | Asafusa et al. | |
| 7,887,487 B2 | 2/2011 | Hao et al. | |
| 2007/0282203 A1 | 12/2007 | Baba et al. | |
| 2008/0269612 A1 | 10/2008 | Kunita | |
| 2009/0312636 A1 | 12/2009 | Kunita | |

FOREIGN PATENT DOCUMENTS

| | | |
|---|---|---|
| CN | 86203861 U | 11/1987 |
| EP | 1 695 665 A2 | 8/2006 |
| EP | 1 769 747 A1 | 4/2007 |
| EP | 1 986 020 A2 | 10/2008 |

(Continued)

OTHER PUBLICATIONS

Chinese Office Action dated Feb. 5, 2010, issued in corresponding Chinese Patent Application No. 200810091287.8.

(Continued)

*Primary Examiner* — Michael Rozanski
(74) *Attorney, Agent, or Firm* — Westerman, Hattori, Daniels & Adrian, LLP

(57) ABSTRACT

A transmission wave corresponding to an FM continuous wave having been subjected to an FM modulation processing is transmitted from a transmitting transducer. A pre-amplifier generates a reception RF signal and outputs the reception RF signal to a receiving mixer. The receiving mixer applies orthogonal detection to the reception RF signal to generate a complex signal. A reference signal supplied to each mixer in the receiving mixer is generated based on an FM continuous wave output from an FM modulator. The FM continuous wave output from the FM modulator is delayed by a delay circuit, and one signal is directly supplied to a mixer whereas the other signal is supplied to a mixer via a $\pi/2$ shift circuit. The delay circuit applies a delay processing in accordance with a depth of a target position within a living organism to the FM continuous wave.

17 Claims, 14 Drawing Sheets

FOREIGN PATENT DOCUMENTS

| | | |
|---|---|---|
| JP | 2005-253949 A | 9/2005 |
| JP | 2006-14916 A | 1/2006 |
| JP | 2006-288974 A | 10/2006 |
| JP | 2007330541 A | 12/2007 |
| WO | 2006/043603 A1 | 4/2006 |

OTHER PUBLICATIONS

Masanori Kunita; "Range Measurement in Ultrasound FMCW System," Electronics and Communications in Japan, Part 3; vol. 90; No. 1; 2007; pp. 9-19.

European Search Report dated Jan. 28, 2011, issued in corresponding European Patent Application No. 08007852.0.

Wilhjelm J E et al., "Coherent FM Doppler System", 1989 Ultrasonics Symposium Proceedings, Oct. 3, 1989, pp. 903-906.

European Search Report dated Aug. 14, 2009, issued in related European Patent Application No. 09006912.1.

European Search Report dated Oct. 5, 2009, issued in related European Patent Application No. 09007364.4.

Chinese Office Action dated Mar. 23, 2011, issued in related Chinese Patent Application No. 2009-10143784.2.

Chinese Office Action dated Mar. 24, 2011, issued in related Chinese Patent Application No. 2009-10147985.X.

USPTO Office Action dated Sep. 15, 2011, issued in U.S. Appl. No. 12/480,874.

U.S. Office Action dated Nov. 14, 2011, issued in related U.S. Appl. No. 12/477,266.

COMPARISON TABLE AMONG PHASE SHIFT TYPE FMCW ULTRASOUND DOPPLER SYSTEM (FMCW), PW, AND CW

| COMPARISON ITEM | PW DOPPLER | CW DOPPLER | FMCW DOPPLER | REMARKS |
|---|---|---|---|---|
| SIGNAL TO NOISE RATIO (SNR) | △ | ○ | ○ | DETERMINED BY FREQUENCY BANDWIDTH EXAMPLE: IF PULSE WIDTH AND BANDWIDTH OF PW IS 4 μs AND 250kHz AND BANDWIDTH OF FMCW IS 2.5kHz, IMPROVEMENT DEGREE IS 20dB. |
| POSITION SELECTIVITY | ○ | × | ○ | DETERMINED BY β OF FMCW EXAMPLE: IF β IS 100, POSITION SELECTIVITY IS APPROXIMATELY EQUAL TO PW |
| CLUTTER POWER | ○ | × | ○ | DETERMINED BY β OF FMCW EXAMPLE: IF β IS 100, IMPROVEMENT DEGREE OVER CW IS 20Db |
| TRANSMISSION PEAK POWER | △ | ○ | ○ | EXAMPLE: IF DUTY RATIO OF PW IS 1/100, PEAK POWER RATIO OF FMCW IS 1/100 OR LESS OF PW |
| MAXIMUM MEASURABLE VELOCITY | × | ○ | △ | ALIASING DOPPLER SIGNALS ARE SMALLER THAN REQUIRED DOPPLER SIGNALS IN THE FMCW METHOD |

FIG. 8

ULTRASOUND DIAGNOSTIC APPARATUS

BACKGROUND

1. Technical Field

The present invention relates to an ultrasound diagnostic apparatus, and more particularly to an ultrasound diagnostic apparatus in which a modulated continuous wave is utilized.

2. Related Art

Continuous wave Doppler is a known ultrasound diagnostic apparatus technology in which a continuous wave is employed. In continuous wave Doppler technology, a transmission wave which is formed as a sinusoidal wave of several MHz is continuously radiated into a living organism and a reflection wave from within the living organism is then continuously received. The reflection wave includes Doppler shift information generated by a moving element (e.g. blood flow) within the living organism. Accordingly, by extracting the Doppler shift information and applying frequency analysis to the Doppler shift information, a Doppler waveform which reflects information of velocity of the moving element, for example, can be formed.

Continuous wave Doppler technology in which a continuous wave is utilized is generally superior to Pulse Doppler, in which a pulse wave is utilized, for rapid acquisition of velocity measurements. Under such circumstances, the inventors of the present application have conducted research concerning continuous wave Doppler technology. In one of their achievements, the present inventors proposed the technology concerning Frequency Modulated Continuous wave Doppler (FMCW Doppler) disclosed in JP 2005-253949 A.

On the other hand, use of a continuous wave makes continuous wave Doppler technology less suited towards measuring a position. As such, typical continuous wave Doppler devices (i.e., devices in which the FMCW Doppler is not utilized) were unable to perform position measurement. In this regard, the present inventors proposed, in JP 2006-14916 A, a technology which enabled measurement of a position of a tissue within a living organism, in addition to measurement of the velocity of a tissue within the living organism, by using FMCW Doppler.

The FMCW Doppler technology described in the above-noted publications is a revolutionary technology providing a potential for new forms of ultrasound diagnosis. The present inventors have continued to research and improve this landmark technology.

SUMMARY

The present invention was made in view of the above circumstances, and advantageously provides a technology for acquiring Doppler information from a desired position by using a continuous wave.

In accordance with one aspect of the invention, there is provided an ultrasound diagnostic apparatus comprising a transmission signal processing section which outputs a modulated transmission signal that is a continuous wave having a frequency varied periodically; a transmission/reception section which transmits ultrasound to a living organism based on the modulated transmission signal and receives a reflection wave from the living organism, thereby obtaining a reception signal; a reception signal processing section which applies a demodulation processing to the reception signal by using a reference signal having a waveform that is substantially the same as a waveform of the modulated transmission signal to obtain a demodulated signal; and a Doppler information extraction section which extracts Doppler information from the demodulated signal, wherein a delay processing in accordance with a depth of a target position within the living organism is performed to adjust a delay relationship between the reference signal and the reception signal and the demodulation processing is performed, thereby selectively extracting the Doppler information from the target position.

In the above aspect, as the demodulation processing is performed with respect to a reception signal by using a reference signal, a demodulated signal containing a signal component having a relatively high degree of correlation with the reference signal can be obtained. Further, for performing the demodulation processing, a delay relationship (a relationship in the time axis direction) between the reference signal and the reception signal is adjusted in accordance with the depth of a target position. For example, a phase relationship between the reference signal and the reception signal is adjusted. Consequently, by aligning the phase of the reception signal from the target position with the phase of the reference signal, for example, the reception signal from the target position can be extracted as a signal component having a relatively high correlation to the reference signal. In addition, by extracting Doppler information from the reception signal by using a band-pass filter or a low pass filter, for example, selective extraction of the Doppler information from the target position can be achieved. Here, with the above aspect, it is desirable that the waveform of the reference signal and the waveform of the modulated transmission signal are completely identical. However, the reference signal and the modulated transmission signal may be in a correspondence relationship, in which their waveforms can be considered to be substantially identical.

BRIEF DESCRIPTION OF THE DRAWINGS

Preferred embodiments of the present invention will be described in detail based on the following figures, wherein:

FIG. 8 is a chart indicating certain characteristics of one embodiment of the present invention;

DETAILED DESCRIPTION

Preferred embodiments of the present invention will be described in detail with reference to the accompanying drawings.

Figure 1:
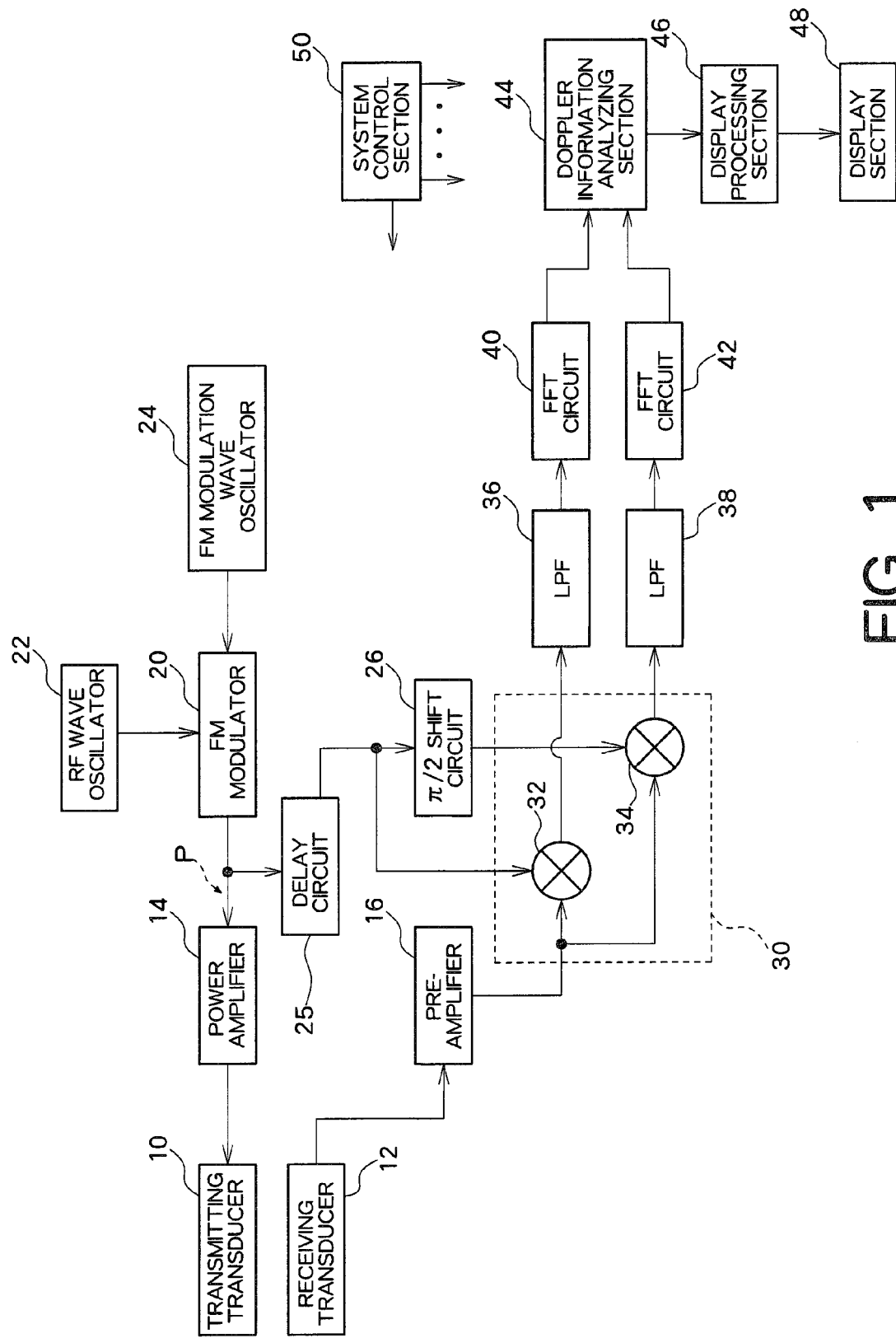
FIG. 1 is a functional block diagram showing the overall structure of an ultrasound diagnostic apparatus according to the present invention.

FIG. 1 is a functional block diagram showing the overall structure of an ultrasound diagnostic apparatus according to a preferred embodiment of the present invention. A transmitting transducer 10 continuously transmits a transmission wave into a living organism, and a receiving transducer 12 continuously receives a reflection wave from within the living organism. Thus, transmission and reception is performed by different transducers, and transmission/reception by means of a so-called continuous wave Doppler method is thus executed.

A power amplifier 14 supplies a power-amplified FM continuous wave (FMCW) to the transmitting transducer 10. An FM continuous wave (FMCW) having been subjected to an FM modulation processing using a sinusoidal wave, for example, is input to the power amplifier 14, and a transmission wave corresponding to this FM continuous wave is then transmitted from the transmitting transducer 10. An FM modulator 20 outputs an FM continuous wave to the power amplifier 14. The FM modulator 20 generates an FM continuous wave based on an RF wave supplied from an RF wave oscillator 22 and a modulation wave which is a sinusoidal wave supplied from an FM modulation wave oscillator 24. The waveform of this FM continuous wave will be described in detail below with regard to explanation of the principle.

A preamplifier 16 applies a reception processing such as low-noise amplification to a reception wave signal supplied from the receiving transducer 12 to generate a receiving RF signal, which is output to a receiving mixer 30. The receiving mixer 30, which is a circuit for applying orthogonal detection to the receiving RF signal to generate a complex baseband signal, is composed of two mixers 32 and 34. Each of the mixers is a circuit which mixes the receiving RF signal with a predetermined reference signal.

The reference signal supplied to each mixer of the receiving mixer 30 is generated based on the FM continuous wave output from the FM modulator 20. Specifically, the FM continuous wave output from the FM modulator 20 is delayed in a delay circuit 25, and the delayed FM continuous wave is directly provided to the mixer 32, whereas the delayed FM continuous wave is supplied to the mixer 34 via a $\pi/2$ shift circuit 26 which shifts the phase of the delayed FM continuous wave by $\pi/2$. Consequently, one of the two mixers 32 and 34 outputs an in-phase signal component (I signal component) and the other outputs a quadrature-phase signal component (Q signal component). Then, high frequency components of the in-phase signal component and the quadrature-phase signal component are removed by LPFs (low pass filters) 36 and 38, respectively, provided downstream of the receiving mixer 30, so that a demodulated signal having only a necessary bandwidth after detection can be extracted.

Here, it is also possible to apply a delay processing to the sinusoidal modulation wave supplied from the FM modulation wave oscillator 24 to thereby form a delayed modulation wave, which is then used for frequency modulation of the RF wave supplied from the RF wave oscillator 22, thereby generating the reference signal.

As will be described in detail in the following explanation of the technological principle of the present invention, a receiving mixer output signal (i.e. a demodulated signal) which is a result of mixing the receiving RF signal with the reference signal performed in each mixer contains a plurality of n-order wave components (n is a natural number which is 0 or greater) concerning a modulation frequency $f_m$ of the modulation wave supplied from the FM modulation wave oscillator 24. Specifically, the receiving mixer output signal contains a direct-current component which is a 0-order wave component, a fundamental component which is the first-order wave component, and also a plurality of harmonic components which are n-order wave components where n is 2 or greater. As such, the demodulated signal containing these plurality of n-order wave components is output from each of the LPFs 36 and 38.

FFT circuits (fast Fourier transform circuits) 40 and 42 execute an FFT operation with respect to each demodulated signal (the in-phase signal component and the quadrature-phase signal component). Consequently, the demodulated signal is transformed into a frequency spectrum in the FFT circuits 40 and 42. Here, the frequency spectrum output from the FFT circuits 40 and 42 is supplied in the form of frequency spectrum data with the frequency resolution $\delta f$, depending on the circuit setting condition or the like. The frequency spectrum output from the FFT circuits 40 and 42 will be described in detail below with reference to FIG. 2 or the like.

A Doppler information analyzing section 44 extracts Doppler information from the demodulated signal which is transformed into the frequency spectrum. At this time, as the phase relationship between the reference signal and the reception signal has been already adjusted in accordance with the depth of a target position within the living organism by the delay circuit 25, Doppler information from the target position can be selectively extracted. The relevance between the phase adjustment and the extraction of Doppler information from the target position will be described in detail while explaining the principle of the present invention. The Doppler information analyzing section 44 extracts the Doppler information for each depth (each position) within the living organism, to thereby compute the velocity of a tissue within the living organism for each depth on the ultrasound beam (sound ray), and outputs the results in real time. Here, the ultrasound beam may be scanned to thereby compute the velocity of the tissue within the living organism at each position in two or three dimensional manner.

A display processing section 46, based on the velocity of the tissue within the living organism for each depth (position), creates a Doppler waveform or a graph including information concerning the depth velocity, for example, and causes a display section 48 to display the Doppler waveform and the graphs thus created in real time. Here, each of the sections in the ultrasound diagnostic apparatus as shown in FIG. 1 is controlled by a system control section 50. Specifically, the system control section 50 performs transmission control, reception control, display control, and so on.

As generally described above, according to the present embodiment, an ultrasound wave (FMCW) which is obtained by applying FM modulation using a modulation wave to a continuous wave (CW) is transmitted and received to obtain a reception signal, and the phase relationship between the reference signal and the reception signal is adjusted in accordance with the depth of a target position within the living organism and then a demodulation processing is performed, so that the Doppler information can be selectively extracted from the target position. Here, the principle for selectively extracting the Doppler information from a target position will be described in detail. First, the fundamental principle of the FMCW which is used in the present embodiment will be described.

An FMCW transmission wave obtained by applying FM modulation to a continuous wave having a frequency $f_0$ by means of a sinusoidal wave with the modulation frequency $f_m$ can be expressed as follows:

$$v_T(t) = \sin(2\pi f_0 t + \beta \sin 2\pi f_m t) \quad \text{[Equation 1]}$$

$$\beta = \frac{\Delta f}{f_m}$$

In the above equation 1, $\Delta f$ is a 0-P value (a zero-peak value: the maximum frequency deviation) of the frequency variation range, and $\beta$, which is a ratio of the maximum frequency deviation $\Delta f$ and the modulation frequency $f_m$, is a modulation index of FM. Further, the FMCW reception wave with no Doppler shift, when attenuation due to the living organism is disregarded, can be expressed as follows:

$$v_R(t) = \sin\{2\pi f_0 t + \phi_0 + \beta \sin(2\pi f_m t + \phi_m)\} \quad \text{[Equation 2]}$$

$$\phi_0 = \frac{4\pi f_0 d}{c}$$

PHASE ANGLE OF RF WAVE $f_0$ CORRESPONDING TO ROUND-TRIP PROPAGATION TIME 2d/c TO AND FROM TARGET
c: PROPAGATION SPEED OF ULTRASOUND $$\phi_m = \frac{4\pi f_m d}{c}$$

PHASE ANGLE OF MODULATION WAVE $f_m$ CORRESPONDING TO ROUND-TRIP PROPAGATION TIME 2d/c TO AND FROM TARGET

The frequency spectrum of the FMCW transmission wave can be obtained by expanding Equation 1 by using Bessel series. The FMCW transmission wave expressed in Equation 1 can be expanded as follows:

$$v_T(t) = \sin 2\pi f_0 t \cdot \cos\{\beta \sin(2\pi f_m t)\} + \quad \text{[Equation 3]}$$
$$\cos 2\pi f_0 t \cdot \sin\{\beta \sin(2\pi f_m t)\}$$
$$= \sin 2\pi f_0 t \left\{ J_0(\beta) + 2\sum_{n=1}^{\infty} J_{2n}(\beta)\cos 2n \cdot 2\pi f_m t \right\} +$$
$$\cos 2\pi f_0 t \cdot 2\sum_{n=0}^{\infty} J_{2n+1}(\beta)\sin\{(2n+1) \cdot 2\pi f_m t\}$$
$$= J_0(\beta)\sin 2\pi f_0 t + \sum_{n=1}^{\infty} J_{2n}(\beta)\{\sin 2\pi (f_0 + 2nf_m t) +$$
$$\sin 2\pi (f_0 - 2nf_m t)\} + \sum_{n=0}^{\infty} J_{2n+1}(\beta)\{\sin 2\pi (f_0 + (2n+1)f_m t) - \sin 2\pi (f_0 - (2n+1)f_m t)\}$$

In Equation 3, $J_0(\beta)$, $J_{2n}(\beta)$, $J_{2n+1}(\beta)$ are Bessel function of the first kind. The amplitude of each term is determined by the modulation index $\beta$ and the corresponding Bessel function.

Further, the frequency spectrum of the reception wave $V_R(t)$ with no Doppler shift can be obtained by expansion of Equation 2. The FMCW reception wave shown in Equation 2 can be expanded as follows:

$$v_R(t) = \sin\{2\pi f_0 t + \phi_0 + \beta \sin(2\pi f_m t + \phi_m)\} \quad \text{[Equation 4]}$$
$$= \sin(2\pi f_0 t + \phi_0) \cdot \cos\{\beta \sin(2\pi f_m t + \phi_m)\} +$$
$$\cos(2\pi f_0 t + \phi_0) \cdot \sin\{\beta \sin(2\pi f_m t + \phi_m)\}$$
$$= \sin(2\pi f_0 t + \phi_0)\{J_0(\beta) +$$
$$2\sum_{n=1}^{\infty} J_{2n}(\beta)\cos 2n(2\pi f_m t + \phi_m)\} +$$
$$\cos(2\pi f_0 t + \phi_0) \cdot 2\sum_{n=0}^{\infty} J_{2n+1}(\beta)\sin\{(2n+1) \cdot$$
$$(2\pi f_m t + \phi_m)\}$$
$$= J_0(\beta)\sin(2\pi f_0 t + \phi_0) + \sum_{n=1}^{\infty} J_{2n}(\beta)$$
$$\{\sin 2\pi((f_0 + 2nf_m)t + \phi_0 + \phi_m) +$$
$$\sin 2\pi((f_0 - 2nf_m)t + \phi_0 - \phi_m)\} +$$
$$\sum_{n=0}^{\infty} J_{2n+1}(\beta)\{\sin 2\pi((f_0 +$$
$$(2n+1)f_m)t + \phi_0 + \phi_m) - \sin 2\pi((f_0 -$$
$$(2n+1)f_m)t + \phi_0 - \phi_m)\}$$

As indicated by Equation 4, the frequency spectrum of a reception wave and the frequency spectrum of a transmission wave have the same frequency components. However, the amplitude of each frequency component of the reception wave varies in accordance with phase differences $\phi_0$ and $\phi_m$.

Further, when Doppler shift is included, $V_R(t)$ in Equation 2 can be rewritten as follows:

$$v_R(t) = \sin\{2\pi(f_0 + f_d)t + \phi_0 + \beta \sin(2\pi f_m t + \phi_m)\} \quad \text{[Equation 5]}$$

Here, in Equation 5, the Doppler shift with regard to $f_m$, which is smaller than a shift amount $f_d$ of $f_0$, is disregarded.

The reception waveforms expressed in Equations 2 and 5 described above are signal waveforms received by the ultrasound transducer (a receiving RF signal). The ultrasound diagnostic apparatus executes a demodulation processing with respect to the receiving RF signal. When demodulating the FMCW receiving RF signal, the demodulation system multiplies the reference signal by the reception wave, using the FMCW transmission wave as the reference signal. The receiving mixer output in the demodulation system is calculated as a result of multiplication of $V_T(t)$ and $V_R(t)$ as follows:

$$v_D(t) = \sin(2\pi f_0 t + \beta \sin 2\pi f_m t) \times \quad \text{[Equation 6]}$$
$$\sin\{2\pi(f_0 + f_d)t + \phi_0 + \beta \sin(2\pi f_m t + \phi_m)\}$$
$$= 1/2\cos\{-2\pi f_d t + \beta \sin 2\pi f_m t -$$
$$\beta \sin(2\pi f_m t + \phi_m) - \phi_0\} -$$
$$1/2\cos\{2\pi(2f_0 + f_d)t + \beta \sin 2\pi f_m t +$$

-continued $$\beta\sin(2\pi f_m t + \phi_m) + \phi_0\}$$

$$\approx 1/2\cos\{-2\pi f_d t + \beta\sin 2\pi f_m t - \beta\sin(2\pi f_m t + \phi_m) - \phi_0\}$$

$$= 1/2\cos\{-2\beta\cos(2\pi f_m t + \phi_m/2) \times \sin(\phi_m/2) - 2\pi f_d t - \phi_0\}$$

$$= 1/2\cos\{k\beta\cos(2\pi f_m t + \phi_m/2) + 2\pi f_d t + \phi_0\}$$

$$k = 2\sin(\phi_m/2)$$

Here, the following mathematical formula concerning the Bessel function is utilized for calculation of Equations 3, 4, and 6.

$$\cos(\beta\cos x) = J_0(\beta) + \sum_{n=1}^{\infty} (-1)^n J_{2n}(\beta)\cos 2nx \quad \text{[Equation 7]}$$

$$\sin(\beta\cos x) = 2\sum_{n=0}^{\infty} (-1)^n J_{2n+1}(\beta)\cos(2n+1)x$$

When the mathematical formula in Equation 7 is used, Equation 6 can be further calculated as follows. Here, in the following Equation 8, a coefficient of ½ in Equation 6 is omitted.

$$v_D(t) = \cos\left\{k\beta\cos\left(2\pi f_m t + \frac{\phi_m}{2}\right) \times \cos(2\pi f_d t + \phi_0)\right\} - \sin\left\{k\beta\cos\left(2\pi f_m t + \frac{\phi_m}{2}\right)\right\} \times \sin(2\pi f_d t + \phi_0) \quad \text{[Equation 8]}$$

$$= (\cos 2\pi f_d t + \phi_0)\{J_0(k\beta) + 2\sum_{n=1}^{\infty}(-1)^n\cos 2n\left(2\pi f_m t + \frac{\phi_m}{2}\right)J_{2n}(k\beta)\} - \sin(2\pi f_d t + \phi_0)\{2\sum_{n=0}^{\infty}(-1)^n\cos(2n+1)\left(2\pi f_m t + \frac{f_m}{2}\right)J_{2n+1}(k\beta)\}$$

$$= \cos(2\pi f_d t + \phi_0)J_0(k\beta) - 2\sin(2\pi f_d t + \phi_0)$$

$$J_1(k\beta)\cos\left(2\pi f_m t + \frac{\phi_m}{2}\right) - 2\cos(2\pi f_d t + \phi_0)$$

$$J_2(k\beta)\cos 2\left(2\pi f_m t + \frac{\phi_m}{2}\right) + 2\sin(2\pi f_d t + \phi_0)$$

$$J_3(k\beta)\cos 3\left(2\pi f_m t + \frac{\phi_m}{2}\right) + 2\cos(2\pi f_d t + \phi_0)$$

$$J_4(k\beta)\cos 4\left(2\pi f_m t + \frac{\phi_m}{2}\right) - 2\sin(2\pi f_d t + \phi_0)$$

$$J_5(k\beta)\cos 5\left(2\pi f_m t + \frac{\phi_m}{2}\right) - 2\cos(2\pi f_d t + \phi_0)$$

$$J_6(k\beta)\cos 6\left(2\pi f_m t + \frac{\phi_m}{2}\right) + 2\sin(2\pi f_d t + \phi_0)$$

$$J_7(k\beta)\cos 7\left(2\pi f_m t + \frac{\phi_m}{2}\right) + 2\cos(2\pi f_d t + \phi_0)$$

$$J_8(k\beta)\cos 8\left(2\pi f_m t + \frac{\phi_m}{2}\right) - 2\sin(2\pi f_m t + \phi_0)$$

$$J_9(k\beta)\cos 9\left(2\pi f_m t + \frac{\phi_m}{2}\right) + \ldots$$

Figure 2:
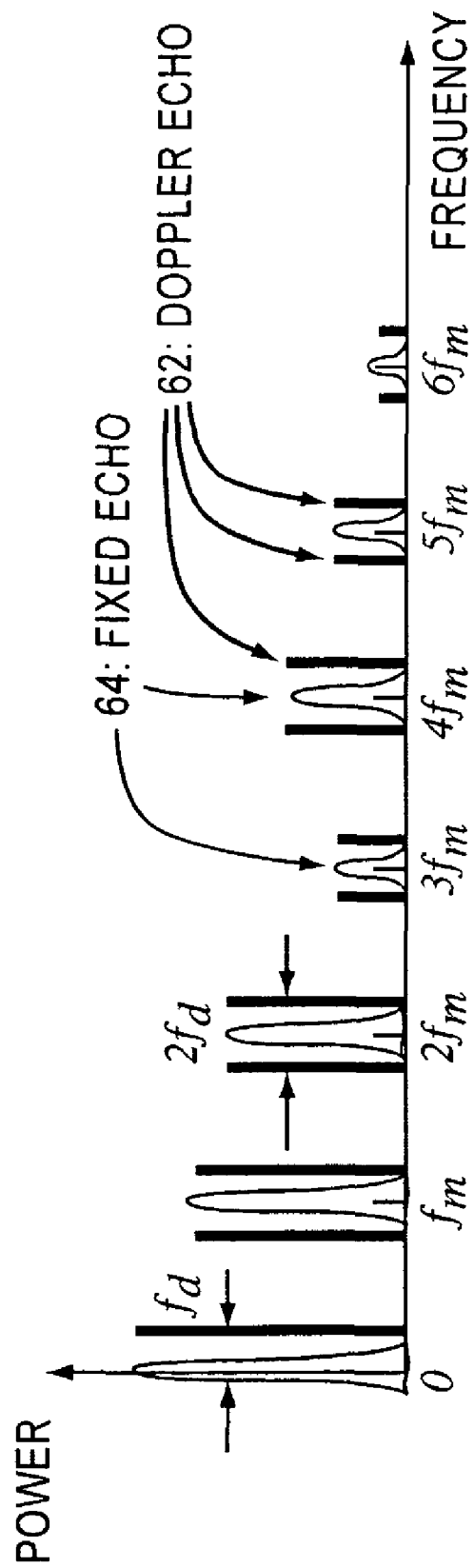
FIG. 2 is a view showing the frequency spectrum of fixed echo and Doppler echo of a demodulated signal (baseband signal)

The frequency spectrum of the receiving mixer output which is expressed by Equation 8, that is the frequency spectrum output from the FFT circuits 40 and 42 in FIG. 1, are shown in FIG. 2.

FIG. 2 is a schematic view showing the frequency spectrum of a demodulated signal. As also indicated in Equation 8, the demodulated signal includes a plurality of n-order harmonic components (n is a natural number which is 0 or greater) concerning the modulation frequency. More specifically, in FIG. 2, the demodulated signal includes a direct-current component which is the 0-order wave component existing near the origin O, the fundamental component ($f_m$) which is the first order wave component, the second harmonic component ($2f_m$) which is the second order wave component, and the third harmonic component ($3f_m$) which is the third order wave component. Further, the demodulated signal also includes the seventh or higher order harmonic components which are not shown. Each of the n-order wave component contains a fixed echo 64 and a Doppler echo 62.

The fixed echo 64 is echo (clutter echo) from a still object which is a strong reflector within the living organism and is an obstruction factor when observing the Doppler information. On the other hand, the Doppler echo 62 is a Doppler signal, which is required. When Doppler shift is involved, each of the n-order wave components of a Doppler signal appears on the frequency spectrum in the form of DSB-SC (Double Sideband-Suppressed Carrier) in which the FM modulation frequency is suppressed. It should be noted that Equations 1 to 8 described above and FIG. 2 are described in JP 2000-253949 A.

The present embodiment is an application of the fundamental principle of FMCW described above. In the present embodiment, the phase relationship between the reference signal and the reception signal is adjusted in accordance with the depth of a target position within a living organism by means of the delay circuit 25 (a phase shifter or a delay line) shown in FIG. 1, so that Doppler information from the target position (i.e. the target depth) can be selectively extracted. More specifically, by setting the delay time of the delay processing performed by the delay circuit 25 to a round-trip propagation time of ultrasound within the living organism, the highest possible degree of correlation can be obtained between the reception signal from the target depth and the reference signal, so that only a signal from the target can be selectively extracted.

Figure 3:
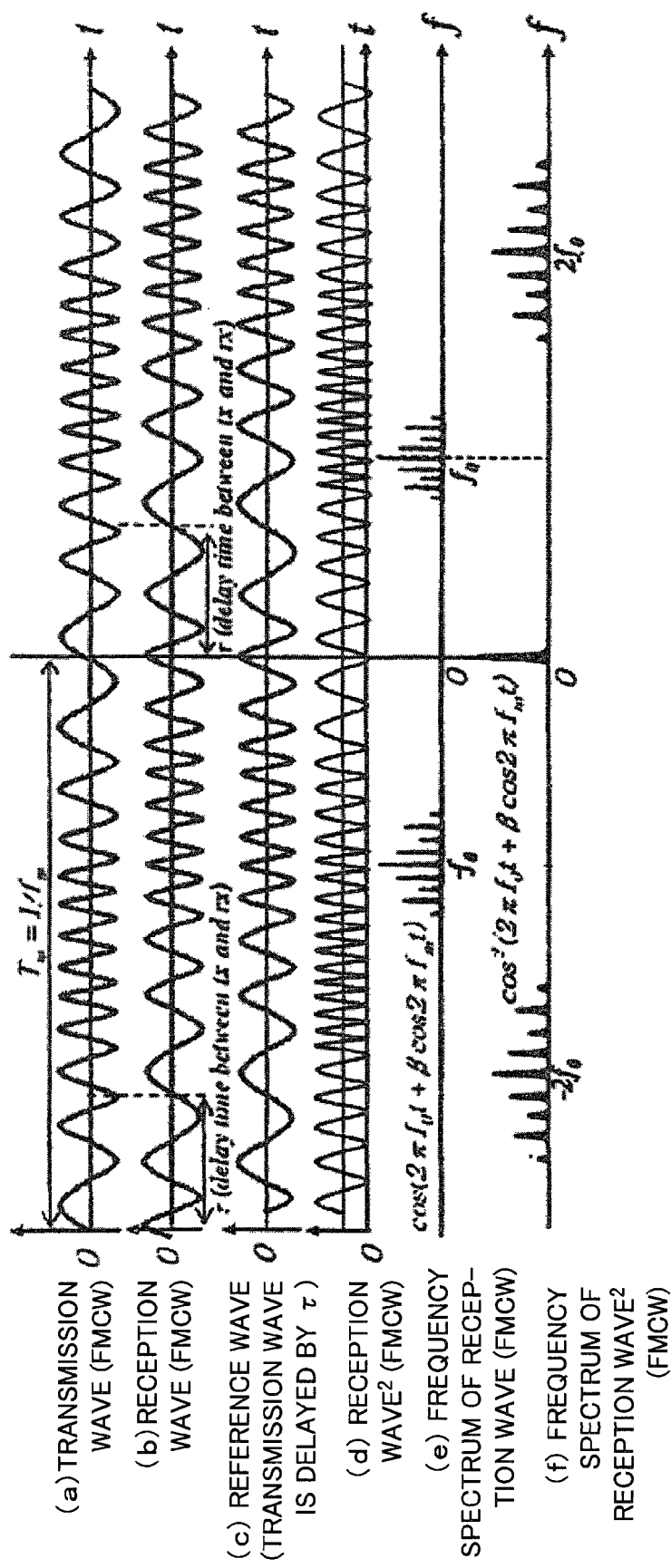
FIG. 3 is a view showing the phase relationship between a reference signal and a reception signal and the frequency spectrum of a baseband signal.

FIG. 3 is a view for explaining the phase relationship (time relationship) between the reference signal and the reception signal. More specifically, FIG. 3(a) shows the time waveform of an FMCW transmission signal (a transmission wave), and FIG. 3(b) shows a reception signal (a reception wave) corresponding to the transmission signal. The reception signal is received with a delay time corresponding to τ from the transmission time. Assuming that the speed of sound is c, the reception signal obtained from the depth d is received with a delay of τ=2d/c. Further, in FIG. 3, $f_0$ indicates a carrier frequency (corresponding to an ultrasound frequency), and $f_m$ indicates a frequency for modulating the carrier (i.e. the modulation frequency). The frequency spectrum power of the reception signal is shown in FIG. 3(e). Here, while the frequency spectrum of the transmission signal, when expressed in the form of power, assumes the same waveform as that shown in FIG. 3(e), the phase of each power spectrum differs from the transmission spectrum in accordance with the delay time τ.

The reference wave (i.e. the reference signal) shown in FIG. 3(c) which orthogonally-detects the reception signal is a signal obtained by shifting the transmission wave by a transmission/reception time difference (i.e. round-trip propagation time τ). The input to the orthogonal detector, i.e. the reception signal and the reference signal input to the receiving mixer (indicated by numeral 30 in FIG. 1) will have a time waveform with the completely identical frequency and phase as a result of this shift operation. Accordingly, the waveform obtained by squaring the reception wave (i.e. the reception signal) is output from the orthogonal detector (i.e. the orthogonal detector output shown in FIG. 3(d)). Hereinafter, this orthogonal detector output signal will be referred to as a baseband signal. The baseband signal can be expressed as a sum of the direct current component with amplitude of ½ and an FM signal with the carrier frequency of $2f_0$ and the modulation degree of $2\beta$. As such, with the square of the reception wave, the reception wave is shifted to the frequency band which is near the direct current and is double the carrier, as shown by the frequency spectrum of the baseband signal in FIG. 3(f).

When the delay time of the reception wave is completely the same as that of the reference wave, the fundamental component $f_m$ and the harmonic components (see FIG. 2) do not appear in the baseband signal, and the baseband signal includes only a direct current component as shown in FIG. 3(f). It should be noted that the components $2f_0$ and $-2f_0$ in FIG. 3(f) are to be removed by the LPFs (indicated by numerals 36 and 38 in FIG. 1) provided downstream of the receiving mixer, for example. On the other hand, if the delay times do not correspond to each other between the reception wave and the reference wave, due to this time difference, harmonic components of the modulation wave, i.e., the fundamental component $f_m$ and the harmonic components (see FIG. 2) are generated. The harmonic components will be generated even when a time difference between the reception wave and the reference wave deviates from "0" by only a slight amount.

Based on the characteristics described above, according to the FMCW method of the present embodiment, the phase relationship between the reception wave (the reception signal) and the reference wave (the reference signal) is adjusted, whereby the velocity information of a target tissue can be obtained based on the signal components of the direct current and near the direct current of the baseband signal. In this sense, the ultrasound diagnostic apparatus according to the present embodiment can be referred to as a phase shift FMCW ultrasound Doppler system.

Figure 4:
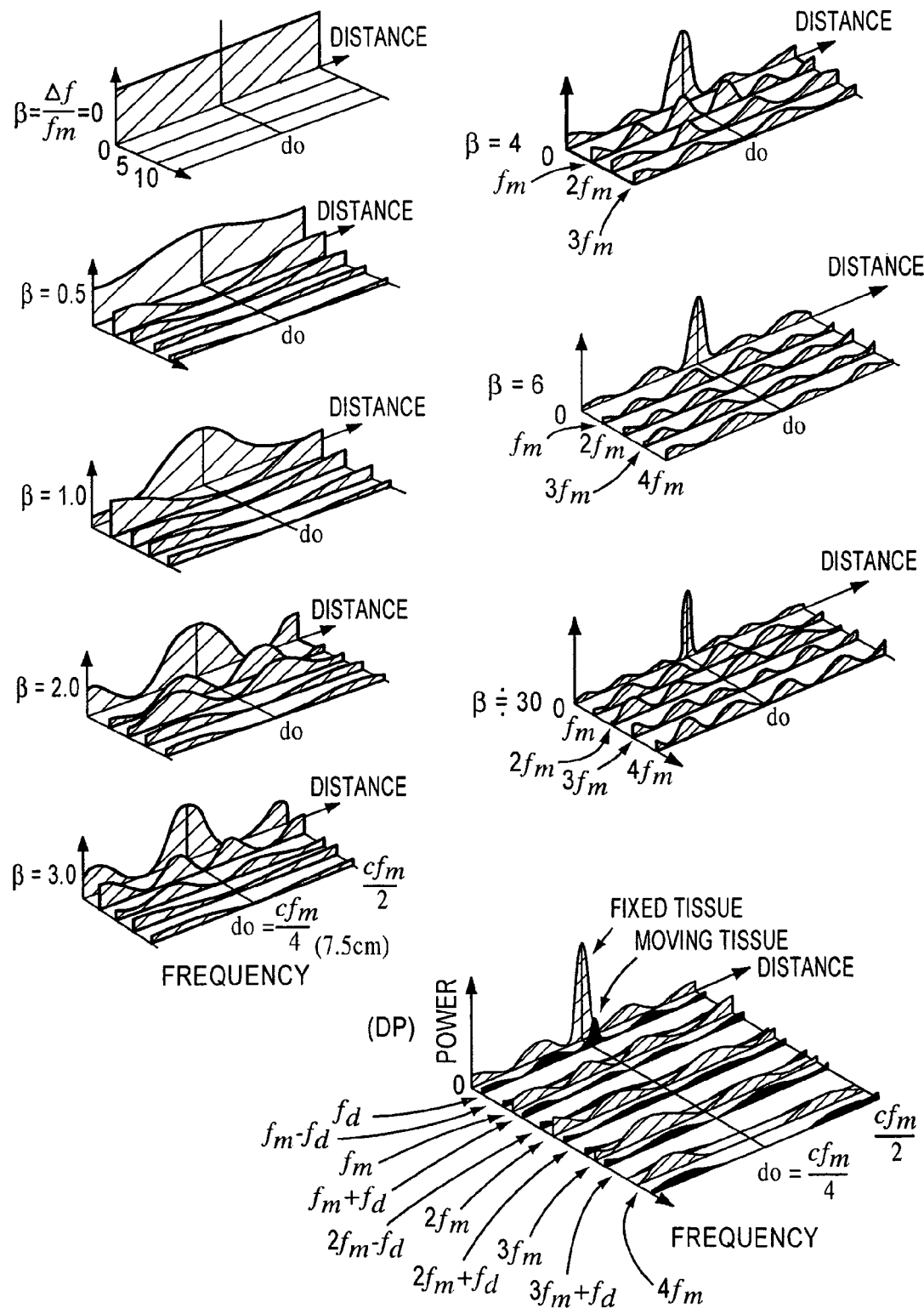
FIG. 4 is a view for explaining dependency of the baseband signal electric power on depth.

FIG. 4 is a view for explaining the dependency of the direct current and harmonic components of a baseband signal on the depth within a living organism (i.e. the distance from the body surface). FIG. 4 shows the frequency spectra of a baseband signal (a demodulated signal) for each of a plurality of modulation indexes β. The frequency spectrum for each modulation index β shown in FIG. 4 corresponds to a frequency spectrum obtained by adding a dimension in the distance direction to the representation of the frequency spectrum shown in FIG. 2. Here, the each frequency spectrum concerning from β=0 to β=:30 represents a reflection power from a fixed tissue and moving target. In FIG. 4, the attenuation effect in the tissue is not considered. Here, the magnitude of the FM modulation degree is generally quantified by the modulation index β. Further, β is defined as a ratio between the maximum frequency deviation Δf of the carrier wave due to FM modulation and the modulation frequency $f_m$, and is defined by $\beta=\Delta f/f_m$.

When β=0, meaning that no modulation is performed, the system of the present embodiment is equivalent to a general CW Doppler velocity measurement system. In such a case, the dependency on positions is not found in the reflection powers from any depths. Further, as no modulation is performed for transmission and reception, there is no possibility that a modulation wave component appears in the baseband signal. When FM modulation is applied to a continuous ultrasound (CW) and the frequency deviation Δf is gradually increased, the FMCW transmission/reception wave will be an FM modulated signal, with its power being shifted from the carrier wave to the sideband wave. If there is no difference in the delay time between transmission and reception, a harmonic component of the modulation wave is not generated in the baseband signal (see FIG. 3). In order to prevent a time difference between two inputs to the orthogonal detector (i.e. the reception signal and the reference signal), a delay time corresponding to the delay time of the reflection wave from the target depth may simply be applied to the reference signal.

The example illustrated in FIG. 4 shows a case in which the delay time to be applied to the reference wave is set to correspond to the delay time of the reception wave when the distance is $d_0=7.5$ cm. Consequently, the reflection power from the distance $d_0$ includes only a direct current component, and no harmonic components of the modulation wave are generated. At positions other than $d=d_0$, the degree of correlation between the two signals is less because a time difference is caused between the transmission wave and the reception wave, which in turn results in a decrease in the direct current component and simultaneously resulting in appearance of harmonic components. This phenomenon can be understood by the concept that, when a time difference is caused between (b) and (c) of FIG. 3, a phenomenon in which a difference in the instantaneous frequencies is repeated in a cycle of the modulation frequency occurs.

As the modulation degree (i.e. the modulation index β) increases, the reflection power at the distance $d_0$ varies more sensitively with respect to a position deviation. In other words, selectivity of the reflection power at the distance $d_0$ increases. This tendency becomes more and more noticeable as β increases. FIG. 4 shows this tendency when β is 0 to approximately 30. When β is 30 or greater, this selectivity is close to a function similar to the role of the range gate in the PW (pulse wave) Doppler velocity measuring system.

It is now assumed that the reflection power from the distance $d_0$ involves Doppler shift $f_d$. In this case, while the distance dependency similar to that of the fixed tissue appears, the distance dependency appears with a shift from the direct current component by the Doppler frequency $f_d$. While the Doppler spectrum also appears in both sideband waves of the modulation wave and the harmonic wave, the Doppler echo from the distance $d_0$ includes only a frequency component which is shifted from the direct current component by $f_d$, as shown in FIG. 4(DP).

As shown in FIG. 4(DP), the Doppler echo from the distance $d_0$ includes only the frequency component which is shifted from the direct current component by $f_d$, because the correlation between the reference signal and a Doppler signal is maximized at the frequency which is shifted from the carrier frequency $f_0$ by $f_d$. This Doppler signal appears only near the direct current components and does not appear near the harmonic components ($f_m$, $2f_m$, $3f_m$, . . . ) of the modulation wave. Accordingly, by extracting this component near the direct current component by means of a low pass filter, the Doppler information in which position information is specified can be obtained with SNR (signal-to-noise ratio) similar to that of general CW Doppler system being maintained.

More specifically, by applying a delay processing to the reference signal with a delay time τ (τ=2d/c, c: velocity of sound, d: depth) corresponding to the target depth (position) d by means of the delay circuit 25 shown in FIG. 1, the FFT circuits 40 and 42 of FIG. 1 output the Doppler frequency spectrum information corresponding to FIG. 4(DP), and the Doppler information analyzing section 44 of FIG. 1 extracts the Doppler signal near the direct current component of FIG. 4(DP).

Next, several characteristics concerning the ultrasound diagnostic apparatus (the phase shift FMCW ultrasound Doppler system) according to the present embodiment will be described.

Clutter Power

As the degree of specification of depth (position) information depends on the modulation degree (i.e. the modulation index) β, it is necessary to set β to a great value in order to ensure the necessary position resolution. With β being set to a large value, the position selectivity becomes sharp. Specifically, as shown in FIG. 4, as β increases, a sharp waveform can be obtained at the target distance $d_0$. Consequently, only the reflection power near the distance $d_0$ is significantly reflected in the reception signal. This nature is common for a fixed target and a moving target.

In contrast to the conventional CW method in which the clutter power is a sum of the reflection powers from all the fixed targets on the sound ray, according to the method (the phase shift FMCW) of the present embodiment, in which only the clutter from a selected position is generated, the clutter power can be reduced to an extreme degree.

Figure 5:
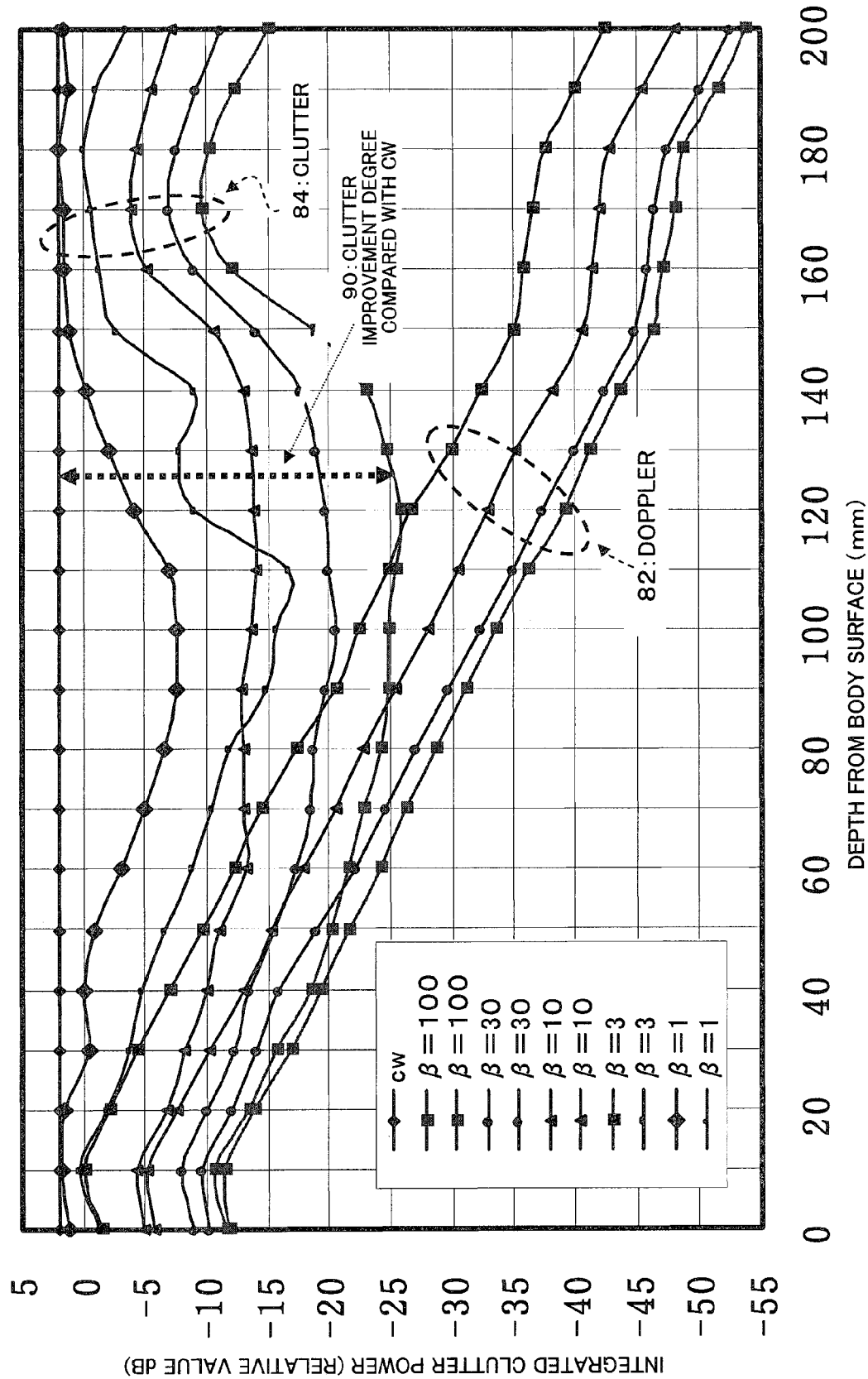
FIG. 5 is a chart of calculation results indicating a relationship between the depth at which Doppler echo is generated and a clutter integral power.

FIG. 5 is a chart of calculation results showing a relationship between the depth (i.e. the depth from the body surface) at which the Doppler echo is generated and the integrated clutter power, with the parameter being the FM modulation index (β). FIG. 5 shows the calculation values of the integrated clutter power 84 and the Doppler signal power 82 for each FM modulation index (β). Further, the clutter improvement degree 90 indicates a reduction in the clutter integral power in comparison with the conventional CW. FIG. 5 shows a tendency in which as the modulation-degree (i.e. the modulation index) β increases, the integrated clutter power is generally decreases. For example, with β=100, the clutter power can be reduced by about 25 dB less than that in the conventional CW.

Signal-to-Noise Ratio (SNR)

Figure 6:
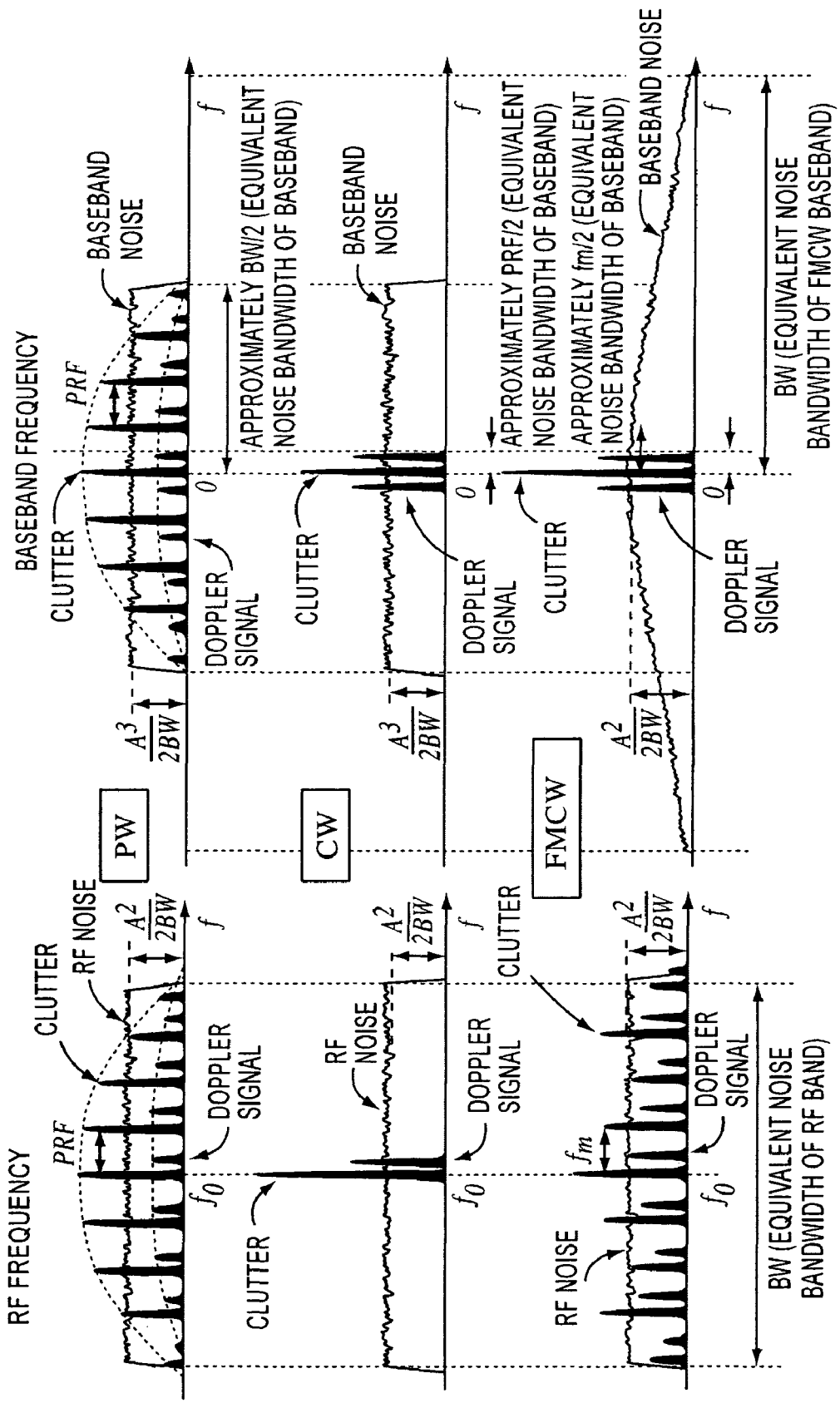
FIG. 6 is a view showing the frequency spectrum of a reception signal and noise in invated FMCW Doppler measuring system.

FIG. 6 shows the spectrum of a reception signal in the RF frequency band and the baseband frequency band concerning the Doppler velocity measurement system of each of the PW (pulse wave), conventional CW, and FMCW. The noise dominating the SNR of PW Doppler is determined by a signal bandwidth at the time of sampling after the orthogonal detection. As in communication systems, this noise can be treated as a white Gauss noise which is distributed in the bandwidth of RF signals. The signal bandwidth at the time of sampling is given by a reciprocal of the pulse width in the baseband. If the pulse width is assumed to be 2 μsec., for example, the bandwidth will be 500 kHz.

On the other hand, in the conventional CW Doppler velocity measurement system, PRF does not exist, and the signal bandwidth is approximately the maximum frequency of the Doppler signal to be measured. If this value is 5 KHz, for example, as the difference in SNR between PW and CW can be expressed by the difference between the bandwidths, the signal bandwidth of CW will be 500 kHz/5 kHz=100. As such, the SNR of CW is improved by 20 dB in comparison with that of PW.

The signal bandwidth of FMCW is determined by the maximum frequency of the Doppler signal in the baseband signal. In FMCW, however, the frequency band which depends on the modulation degree is included in the RF (ultrasound) frequency band, and a signal diffuses in a wide band. However, as this wide band signal is compression-transformed into a narrow band baseband signal near the direct current component due to orthogonal detection, the noise is also in the narrow band, leading to a significant improvement of SNR. The degree of improvement is similar to the case of CW, and in the case of 500 kHz/5 kHz=100 as described above, the improvement of 20 dB compared to the PW can be expected.

Position Selectivity (Position Resolution)

With the PW Doppler, the Doppler information from a specific position can be obtained, however, with the normal CW Doppler method, the position information cannot be obtained. The phase shift FMCW system of the present embodiment is considered to complement these characteristics. In the demodulation process of the present embodiment, the delay time of the reference signal for use in orthogonal detection is matched with the distance to the target, so that the reference signal assumes the position selectivity. This selectivity has a nature that as the modulation index β increases, the selectivity is improved. With the increase in the modulation index β, the bandwidth of the carrier band is expanded. The necessary bandwidth is approximately given by the following equation:

$$BW \approx 2(f_m + \Delta f) = 2(f_m + \beta f_m) = 2f_m(1+\beta)$$ [Equation 9]

Figure 7:
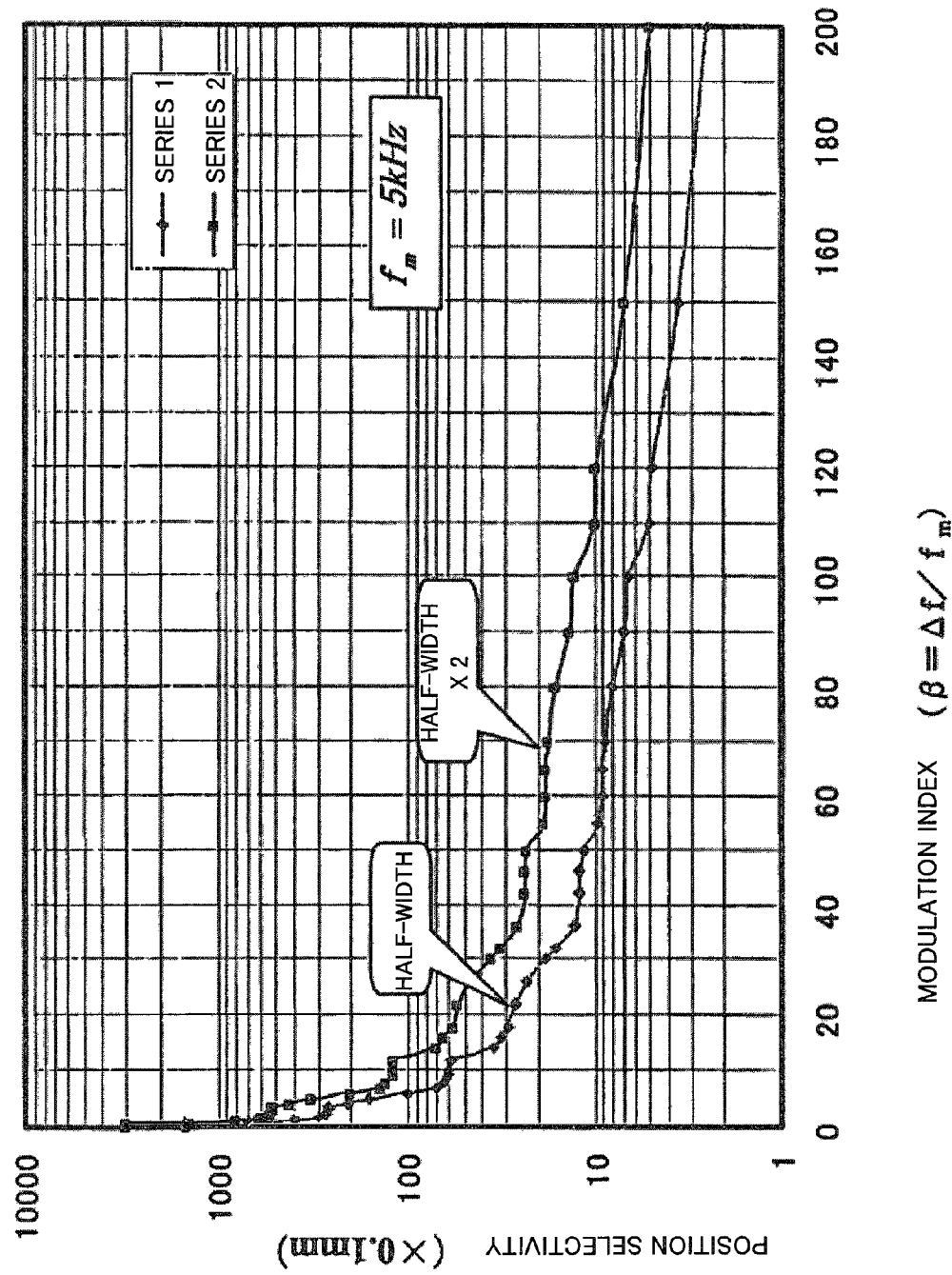
FIG. 7 is a graph showing calculation results of position selectivity in accordance with the modulation index.

FIG. 7 is a chart showing a calculation result of the position selectivity in accordance with the degree of modulation index. The half width shown in FIG. 7 means a half width of the frequency spectrum waveform at a target position (i.e. a half width of the frequency spectrum waveform at the distance $d_0$ of each frequency spectrum shown in FIG. 4).

As shown in FIG. 7, by increasing β, the position selectivity can be set to several mm or less. This result indicates that the wider the frequency band of the carrier wave, the more improved the position resolution of the target. This feature is not inconsistent with the feature concerning PW, that the smaller the pulse width, the greater the improvement in the position resolution in RADAR systems.

As such, according to the phase shift FMCW method of the present embodiment, by setting β to a sufficiently large value which satisfies the desired position resolution, i.e. by setting the bandwidth of FMCW given by Equation 9 to approximately the same bandwidth of PW, Doppler information with position information and a desired SNR can be obtained.

Maximum Blood Flow Velocity

In the FMCW method, as in the PW method, the maximum velocity is limited. In the FMCW method, the carrier wave is modulated with a modulation wave having a frequency of $f_m$, and the maximum measurable frequency is limited to $f_m/2$ due to aliasing. This limitation can be reduced because aliasing doppler signals are smaller than required doppler signals in the FMCW method.

Structure of Transmission/Reception Section

When the average power in the probe input is equal among the PW, CW, and FMCW Doppler velocity measurement systems, the peak power for achieving the improvement effects with regard to the clutter and noise described above can be reduced in the FMCW method of the present embodiment to approximately 1/100 compared with PW, and the peak voltage can be reduced to 1/10. On the other hand, when the transmission power which can be input to the probe is limited by the peak value, in contrast to PW, with the FMCW of the present embodiment, suppression of the clutter and improvement in SNR can be further expected at a ratio which can increase the power, in addition to the improvement effects with regard to the clutter and noise.

A preferred embodiment of the present invention has been described above; some of the characteristics (advantages) of this embodiment are summarized as shown in FIG. 8.

Figure 9:
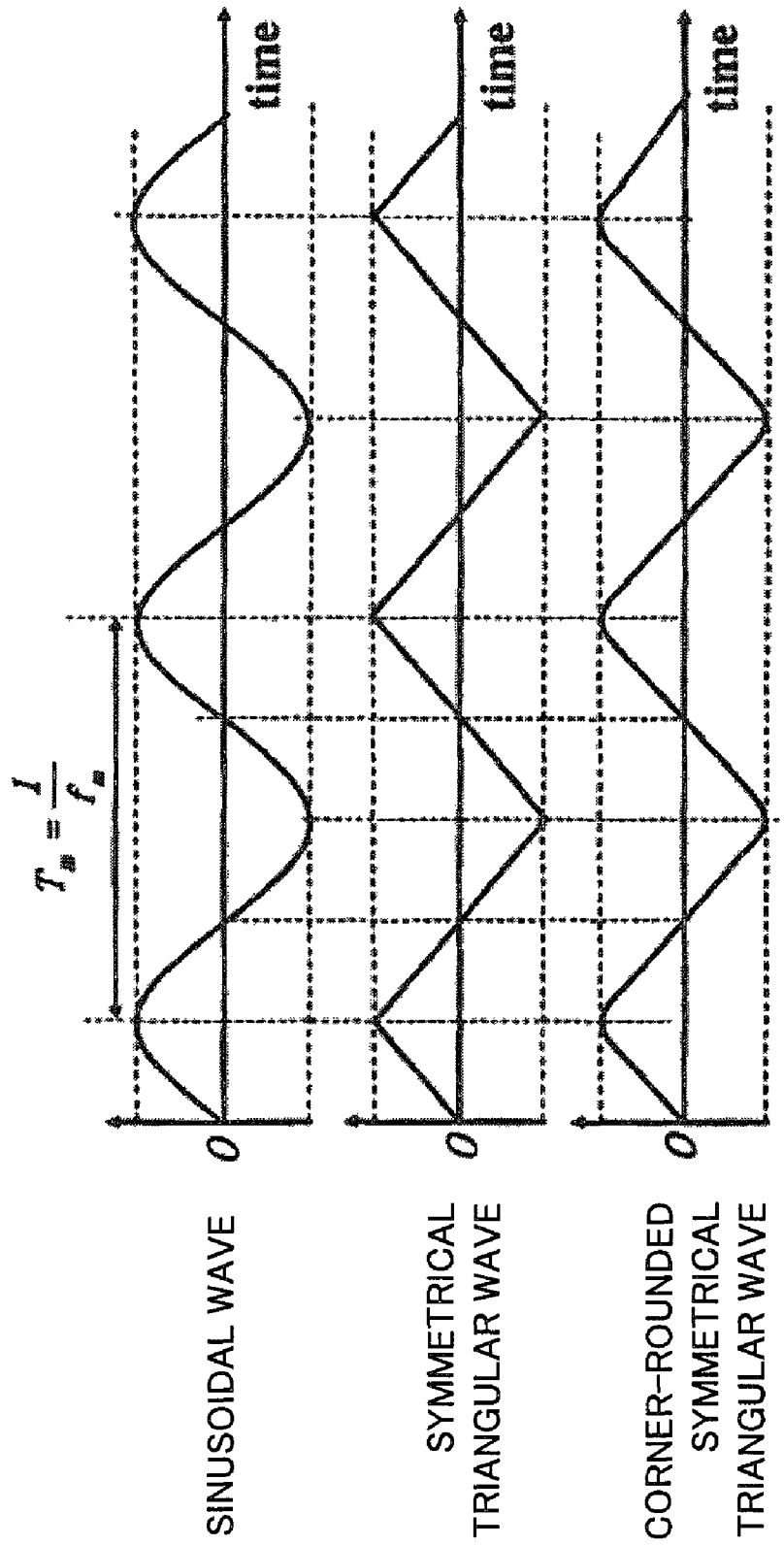
FIG. 9 is a view for explaining the waveform of a modulation wave.

Further, in the embodiment described above, the sinusoidal wave as shown in FIG. 9 is utilized as the modulation wave. In place of this sinusoidal wave, a symmetrical triangular wave as shown in FIG. 9 may be used as the modulation wave. The use of the symmetrical triangular wave is advantageous in that the position information and the Doppler information can be measured separately (see JP 2006-14916 A). Here, as the symmetrical triangular wave has a periodicity which is similar to that of the sinusoidal wave, even if the symmetrical triangular wave is used in place of the sinusoidal wave, the phase shift FMCW ultrasound Doppler system can be configured.

In addition, as shown in FIG. 9, a symmetrical triangular wave in which the frequency change at the conversion point of the modulation frequency change is smoothed in terms of time (i.e. a corner-rounded symmetrical triangular wave) may also be used as the modulation wave. This waveform provides an advantage that high frequency components generated by the symmetrical triangular wave at the conversion point of the modulation frequency change can be removed. In other words, by smoothing the frequency change at this conversion point in terms of time, generation of the high frequency components can be reduced, such that excessive expansion of the RF bandwidth can be advantageously prevented.

Also, as an example variation for adjusting the phases between a reception signal and a reference signal, the delay circuit 25 may be displaced to a position immediately before the power amplifier 14 (i.e. the position indicated by P in FIG. 1) in FIG. 1. In other words, it is possible to apply a delay processing to the transmitting FMCW to be supplied to the power amplifier 14 while applying no delay processing to the reference signal to be supplied to the receiving mixer 30, and to then adjust the phases between the reference signal and the reception signal. Here, a further delay circuit 25 may be provided immediately before the power amplifier 14 while the delay circuit 25 shown in FIG. 1 remains provided. Specifically, it is also possible to apply a delay processing to the transmitting FMCW to be supplied to the power amplifier 14 and further apply a delay processing to the reference signal to be supplied to the receiving mixer 30, and then adjust the phases between the reference signal and the reception signal.

In addition, it is also possible to delay the modulation signal (i.e. the modulation wave) for use in the frequency modulation processing by a delay amount in accordance with the depth of a target position to thereby generate a delayed modulation signal, and then perform a frequency modulation processing with respect to the carrier signal (an RF wave) by using the delayed modulation signal to form a reference signal. Then, the phases of the reception signal and the reference signal are adjusted. In this case, a modulated transmission signal (an FMCW transmission signal) is generated by applying the frequency modulation processing to the carrier signal by using a modulation signal which is not delayed, for example.

With the ultrasound diagnostic apparatus shown in FIG. 1, in which the phase relationship between the reference signal and the reception signal is adjusted in accordance with the depth of a target position within the living organism by the delay circuit 25, the Doppler information from the target position can be selectively extracted. Accordingly, by extracting the Doppler information for each depth (each position) within the living organism, the velocity of a tissue within the living organism can be calculated for each depth on the ultrasound beam (ray of sound), for example. In addition, with the periodic variation in the delay amount in the delay circuit 25, the target position is periodically shifted within a subject section along the ultrasound beam, so that the Doppler information can be extracted from a plurality of positions through the subject section, as will be described below.

Figure 10:
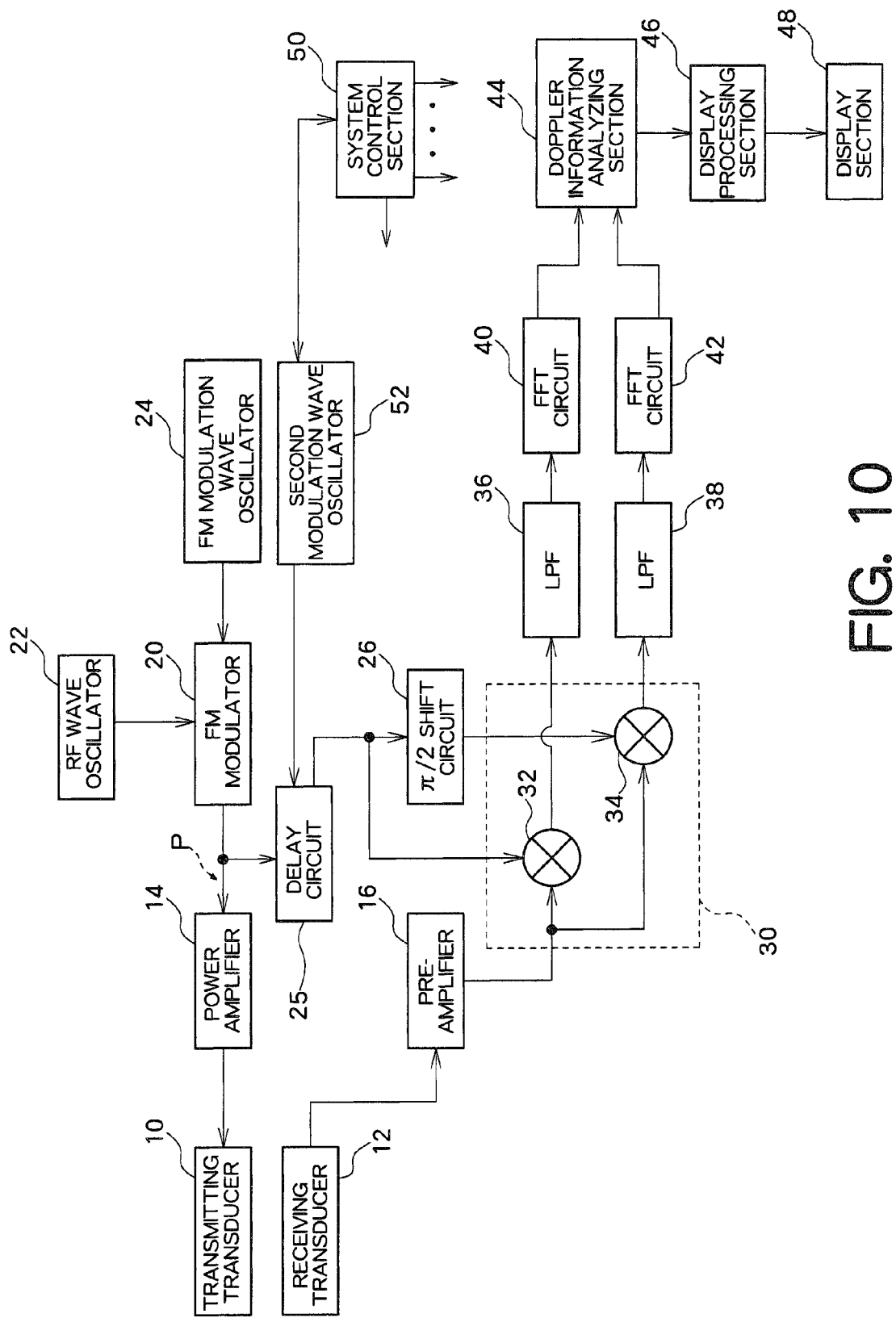
FIG. 10 is a diagram showing another preferred embodiment of an ultrasound diagnostic apparatus according to the present invention.

FIG. 10 is a functional block diagram showing the overall structure of an ultrasound diagnostic apparatus according to another preferred embodiment of the present invention. The ultrasound diagnostic apparatus shown in FIG. 10 is an improved version of the ultrasound diagnostic apparatus shown in FIG. 1, and differs from the apparatus shown in FIG. 1 in that a second modulation wave oscillator 52 is provided. Hereinafter, the ultrasound diagnostic apparatus shown in FIG. 10 will be described mainly with regard to the additional advantages achieved by the provision of the second modulation wave oscillator 52, and description of elements corresponding to those in the apparatus of FIG. 1 will not be repeated.

In the ultrasound diagnostic apparatus shown in FIG. 10, as in the ultrasound diagnostic apparatus shown in FIG. 1, the phase relationship between the reference signal and the reception signal is adjusted in accordance with the depth of a target position within the living organism by means of the delay circuit 25, and the Doppler information from the target position can be selectively extracted. More specifically, by setting the delay time (the delay amount) of the delay processing performed by the delay circuit 25 to the propagation time required for the ultrasound to travel a round trip through the living organism, the correlation between the reference signal and the reception signal from the target depth is maximized, so that a signal from just the target can be selectively extracted.

In FIG. 10, the delay time in the delay circuit 25 is periodically varied to periodically shift the target position within a subject section along the depth direction, whereby the Doppler information is extracted from a plurality of positions throughout the subject section. Here, the delay circuit 25 periodically varies the delay time based on a signal output from the second modulation wave oscillator 52.

The second modulation wave oscillator 52 outputs a second modulation wave having a frequency which is lower than that of the modulation wave (i.e. the first modulation wave) output from the FM modulation wave oscillator 24. If the frequency of the first modulation wave is set to approximately 5 kHz, for example, the frequency of the second modulation wave may be set to approximately 50 Hz, for example. The delay circuit 25 uses this second modulation wave with a relatively low frequency to periodically vary the delay time.

With the periodic variation of the delay time, the target position at which the correlation between the reference signal and the reception signal is the maximum also varies periodically along the ultrasound beam direction (i.e. the depth direction in the living organism). Specifically, the target position is periodically shifted within a certain range (i.e. within the subject section) along the depth direction, so that the Doppler information can be extracted from a plurality of positions through the subject section.

Here, in FIG. 10, as in the case with FIG. 1, the shift circuit 25 may be displaced to a position immediately before the power amplifier 10 (i.e. the position indicated by P in FIG. 10). In other words, it is possible to apply a delay processing with a periodic variation to the transmitting FMCW to be supplied to the power amplifier 14 while applying no delay processing to the reference signal to be supplied to the receiving mixer 30, and then adjust the phases of the reference signal and the reception signal.

The target position which is periodically shifted is determined in accordance with the delay time (delay amount) in the delay circuit 25. The system control section 50 confirms the target position which periodically shifts based on the second modulation wave output from the second modulation wave oscillator 52 or based on the delay time in the delay circuit 52. The system control section 50 then associates the Doppler information (e.g. the Doppler shift amount, the electric power of Doppler components, and so on) obtained in the Doppler information analyzing section 44 with the position (depth) from which the Doppler information is obtained. This correspondence relationship is then provided to the display processing section 46, and so on.

Figure 11:
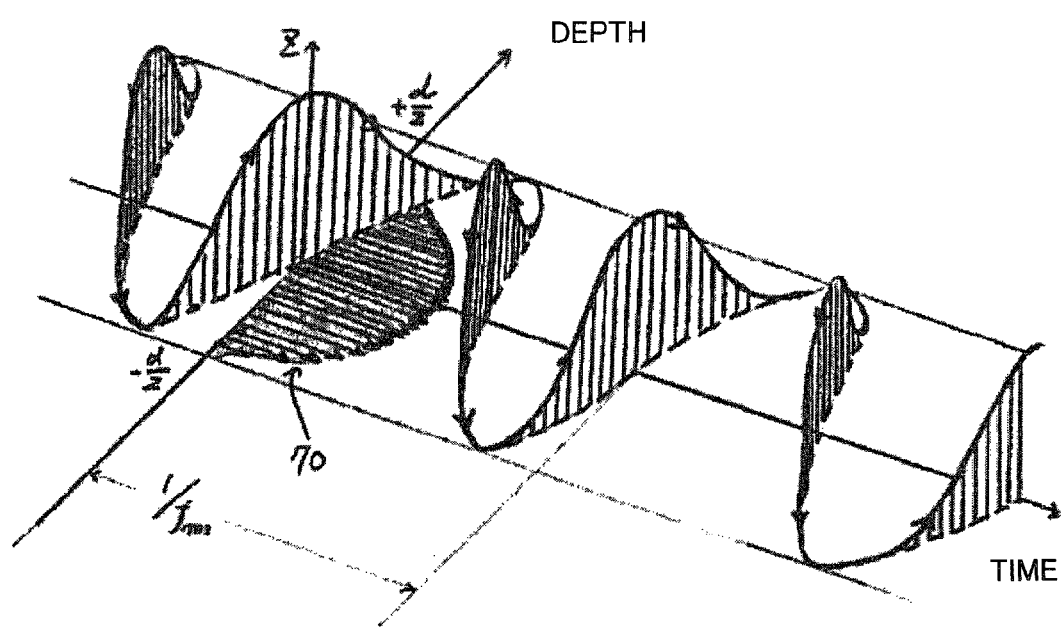
FIG. 11 is a view for explaining a relationship among the Doppler information, depth, and time when the second modulation wave is a sinusoidal wave.

FIG. 11 is a view for explaining the correspondence relationship between the Doppler information and the depth when the second modulation wave is a sinusoidal wave. FIG. 11 shows a graph in which the time axis and the depth axis are provided on the bottom surface and the Doppler information (the Doppler shift amount or the electric power of Doppler components) is indicated in the Z axis in the height direction.

When the second modulation wave is a sinusoidal wave, the delay time in the delay circuit 25 (FIG. 10) varies in a sinusoidal wave form with elapse of time, and the target position (depth) from which the Doppler information can be obtained also varies in a sinusoidal wave form with elapse of time.

FIG. 11 shows a state in which, with elapse of time, the target position varies along the sinusoidal wave between the depth −d/2 and the depth +d/2 (i.e. the subject section). The graph in FIG. 11 shows an example case in which the frequency of the second modulation wave is $f_{m2}$, in which case the target position varies along the sinusoidal wave having a period of $1/f_{m2}$. Further, at each of the positions which vary along the sinusoidal wave, the Doppler information obtained from the corresponding position is indicated in the Z-axis direction.

As described above, as the Doppler information can be obtained for each position within the subject section from the depth −d/2 to the depth +d/2, the velocity distribution 70 within the subject section from the depth −d/2 to the depth +d/2 can be obtained as shown in FIG. 11, by calculating the velocity for each position (depth) from the Doppler information.

It should be noted that, in FIG. 11, a relatively great amount of Doppler information is obtained at an intermediate position between the depth −d/2 and the depth +d/2. In the blood vessel, a larger amount of blood flow can be obtained at the center of the blood vessel than in the vicinity of the blood vessel wall. Accordingly, by setting the ultrasound beam so as to be orthogonal to the blood vessel and setting the subject section (from the depth −d/2 to the depth +d/2) in a portion on the ultrasound beam corresponding to the blood vessel, the measurement result as shown in FIG. 11, for example, can be obtained, and the velocity distribution 70 of the blood flow within the blood vessel can be obtained.

Figure 12:
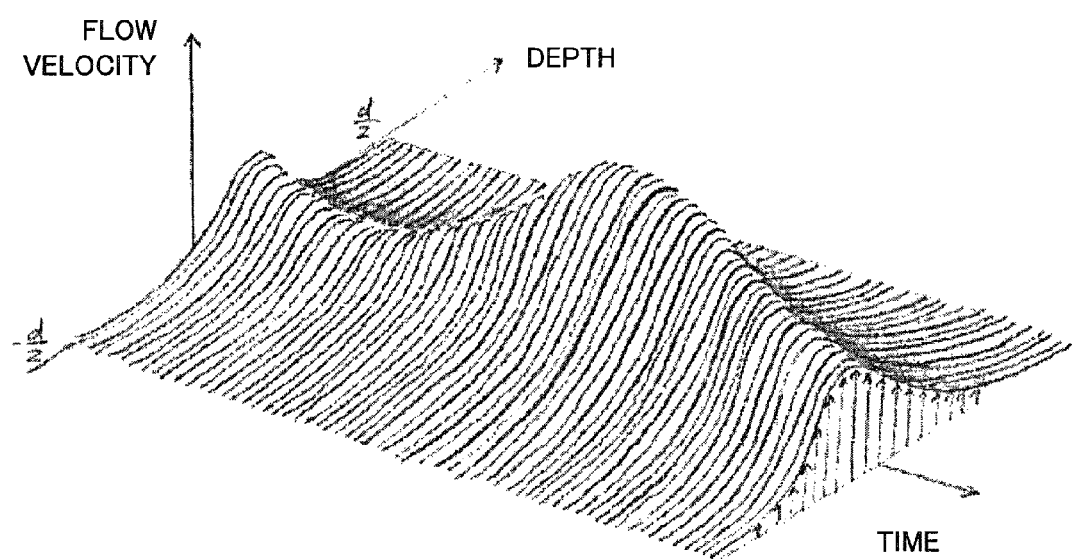
FIG. 12 is a view showing a display mode of velocity distribution.

FIG. 12 is a view showing a display mode of the velocity distribution, and shows a graph in which the time axis and the depth axis are provided on the bottom surface and the velocity obtained from the Doppler information is indicated in the height direction. The graph shown in FIG. 12 is an example of an image formed by the display processing section 46 and displayed on the display section 48 (see FIG. 10). The display processing section 46 forms the image shown in FIG. 12 based on the correspondence relationship between the Doppler information and the position (depth) obtained from the system control section 50, for example.

Specifically, the target position (depth) which is shifted with elapse of time and the Doppler information obtained from the Doppler information analyzing section 44 of FIG. 10 are associated with each other, whereby the velocity (i.e. the flow velocity) is calculated from the Doppler information. Then, with the repetitious shifting of the target position within the subject section from the depth −d/2 to the depth +d/2 with elapse of time, the graph shown in FIG. 12 showing the variation in the flow velocity with time within the subject section is formed.

The graph of FIG. 12 shows a state in which the flow velocity distribution within the subject section from the depth −d/2 to the depth +d/2 varies with elapse of time. For example, by setting the ultrasound beam so as to be orthogonal to the blood vessel and setting the subject section (from the depth −d/2 to the depth +d/2) in a portion on the ultrasound beam corresponding to the blood vessel, the measurement result as shown in FIG. 12 can be obtained as a variation of the flow velocity distribution of the blood flow in that blood vessel portion.

Here, while a case in which the second modulation wave is a sinusoidal wave has been described with references to FIGS. 11 and 12, the second modulation wave may be a sawtooth wave or a triangular wave.

Figure 13:
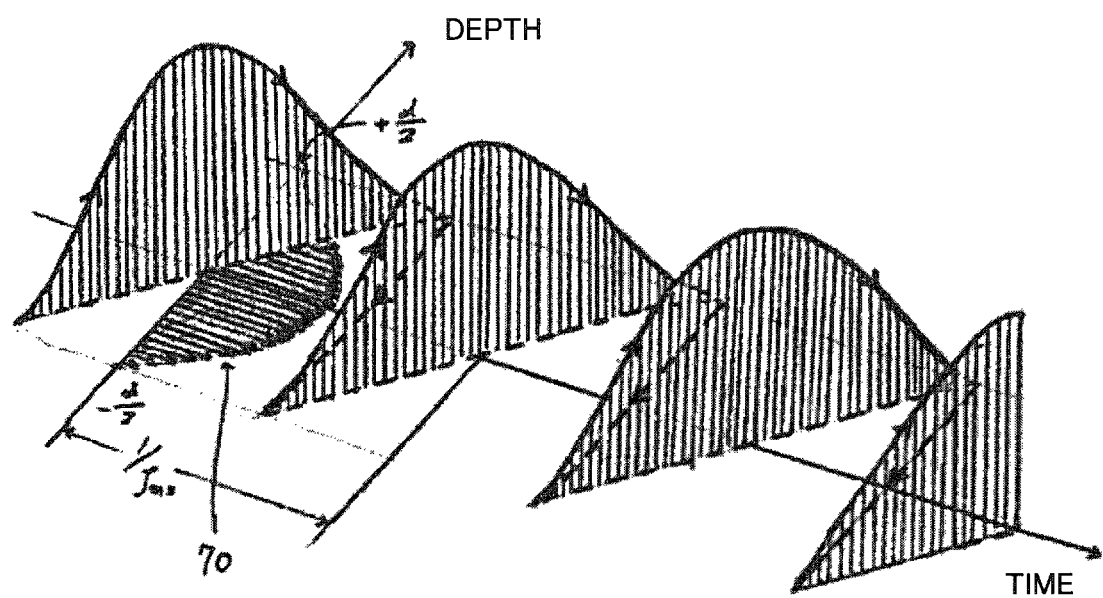
FIG. 13 is a view for explaining a correspondence relationship between the Doppler information and the depth when the second modulation wave is a sawtooth wave.

FIG. 13 is a view for explaining the correspondence relationship between the Doppler information and the depth when the second modulation wave is a sawtooth wave. Specifically, FIG. 13, similar to FIG. 11, shows a graph in which the time axis and the depth axis are provided on the bottom surface and the Doppler information is indicated in the height direction. When the second modulation wave is a sawtooth wave, the delay time in the delay circuit 25 (FIG. 10) varies in a sawtooth wave shape with elapse of time, and the target position (depth) from which the Doppler information is obtained also varies in a sawtooth wave shape with elapse of time.

FIG. 13 shows a state in which the target position varies along the sawtooth wave between the depth −d/2 and the depth +d/2 (i.e. the subject section) with elapse of time. Here, in the graph shown in FIG. 13, similar to the graph shown in FIG. 11, the frequency of the second modulation wave is $f_{m2}$, and the target position varies along the sawtooth wave having a frequency of $1/f_{m2}$. Then, at each of the positions which vary along the sawtooth wave, the Doppler information obtained from the corresponding position is indicated in the height direction. Additionally, as in the case of FIG. 11, the velocity distribution 70 within the subject section from the depth −d/2 to the depth +d/2 may be obtained.

Figure 14:
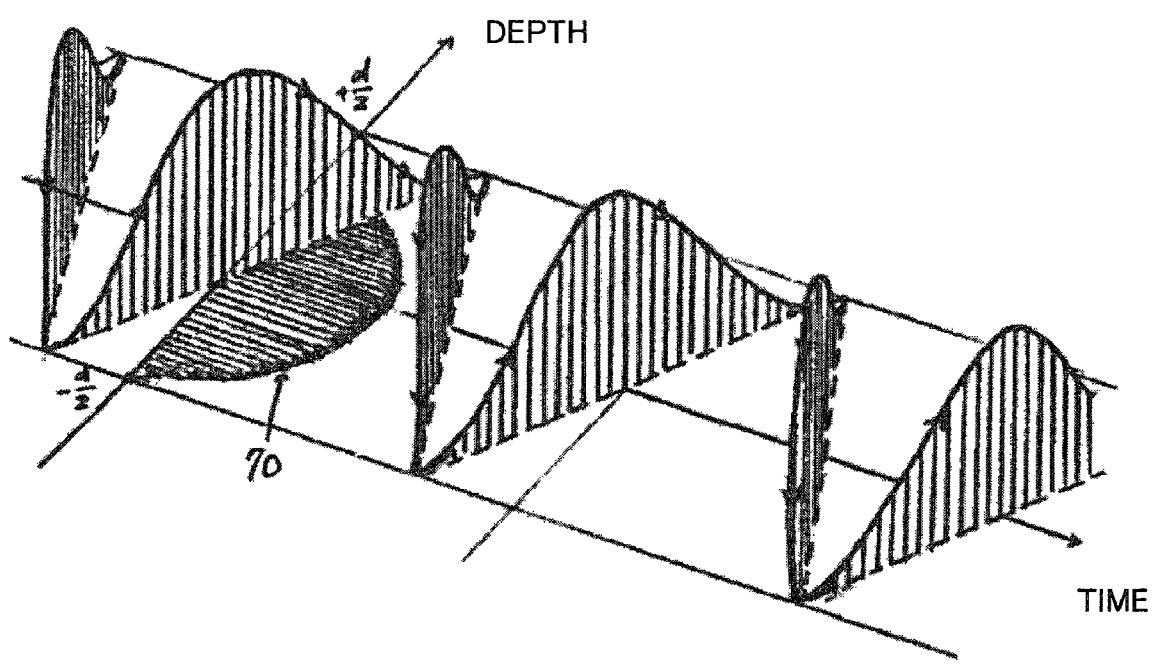
FIG. 14 is a view for explaining a correspondence relationship between the Doppler information and the depth when the second modulation wave is a symmetrical triangular wave.

FIG. 14 is a view for explaining the correspondence between the Doppler information and the depth when the second modulation wave is a symmetrical triangular wave. Specifically, FIG. 14, similar to FIGS. 11 and 13, shows a graph in which the time axis and the depth axis are provided on the bottom surface and the Doppler information is indicated in the height direction. When the second modulation wave is a symmetrical triangular wave, the target position (depth) from which the Doppler information is obtained varies along a symmetrical triangular wave shape with elapse of time. In FIG. 14, at each of the positions which vary along the symmetrical triangular wave, the Doppler information obtained from the corresponding position is indicated in the height direction. Further, as in the cases of FIGS. 11 and 13, the velocity distribution 70 within the subject section from the depth −d/2 to the depth +d/2 may be obtained.

While example preferred embodiments of the present invention and some modification examples have been described, the preferred embodiments or the like described above are provided only for illustrative purposes, and therefore do not limit the scope of the present invention. It should therefore be understood that the present invention includes various modifications within the range of the nature of the present invention.

For example, in the embodiments described above, when forming a modulated transmission signal that is a continuous wave having a frequency periodically varied, a frequency modulation processing is applied to a carrier wave signal (i.e. an RF wave supplied from the RF wave oscillator 22). In place of this frequency modulation processing, a phase modulation processing (PM processing), which is obvious to a person with ordinary skill in the art as an angle modulation method similar to the frequency modulation processing, may alternatively be used. More specifically, a waveform which is the same as or equivalent to the FM continuous wave output from the FM modulator 20 may be formed by applying the phase modulation processing to the carrier signal (i.e. an RF wave supplied form the RF wave oscillator 22). Here, it is possible to store the data of a continuous wave with periodically varying frequencies in a memory or the like and generate the continuous wave based on the data which is read from this memory.

That is, while the preferred embodiments of the present invention have been described using specific terms, such description is for illustrative purposes only, and it is to be understood that changes and variations may be made without departing from the spirit or scope of the appended claims.

What is claimed is:

1. An ultrasound diagnostic apparatus comprising:
    a transmission signal processing section which outputs a modulated transmission signal that is a continuous wave having a frequency varied periodically;
    a transmission/reception section which transmits ultrasound to a living organism based on the modulated transmission signal and receives a reflection wave from the living organism, thereby obtaining a reception signal;
    a reception signal processing section which applies a demodulation processing to the reception signal by using a reference signal having a waveform that is substantially the same as a waveform of the modulated transmission signal to obtain a demodulated signal;
    a delay processing section which adjusts a delay relationship between the reference signal and the reception signal; and
    a Doppler information extraction section which extracts Doppler information from the demodulated signal,
    wherein
    the delay processing section performs a delay processing in accordance with a depth of a target position within the living organism to adjust the delay relationship between the reference signal and the reception signal and the demodulation processing is performed, thereby selectively extracting the Doppler information from the target position.

2. The ultrasound diagnostic apparatus according to claim 1, wherein
    at least one of the modulated transmission signal output from the transmission signal processing section and the reference signal to be used in the reception signal processing section is delayed to enhance a correlation between the reception signal from the target position and the reference signal, thereby selectively extracting the Doppler information from the target position.

3. The ultrasound diagnostic apparatus according to claim 2, wherein
    the at least one of the modulated transmission signal and the reference signal is delayed such that a phase of the reception signal from the target position and a phase of the reference signal are identical.

4. The ultrasound diagnostic apparatus according to claim 3, wherein
    the modulated transmission signal or the reference signal is delayed by a delay amount in accordance with a depth of the target position such that a phase of the reception signal from the target position and a phase of the reference signal are identical.

5. The ultrasound diagnostic apparatus according to claim 4, wherein
    the Doppler information is extracted from the target position while varying the delay amount to thereby shift the target position along a depth direction.

6. The ultrasound diagnostic apparatus according to claim 5, wherein
    the Doppler information is extracted from a plurality of positions through a subject section along the depth direction, by periodically varying the delay amount to thereby periodically shift the target position within the subject section along the depth direction.

7. The ultrasound diagnostic apparatus according to claim 6, wherein
    a velocity distribution of a fluid within the subject section is formed based on the Doppler information extracted from the plurality of positions in the subject section.

8. The ultrasound diagnostic apparatus according to claim 7, wherein
    a display image which includes an axis corresponding to a depth within the living organism, an axis corresponding to time, and an axis corresponding to a velocity of the fluid and which shows a state of a variation in the velocity distribution with time is formed.

9. The ultrasound diagnostic apparatus according to claim 1, wherein
    the Doppler information extraction section extracts, as the Doppler information, a Doppler signal component corresponding to a direct current signal component which is contained in the demodulated signal.

10. The ultrasound diagnostic apparatus according to claim 1, wherein
    the transmission signal processing section applies a frequency modulation processing to a carrier wave signal to generate the modulated transmission signal.

11. The ultrasound diagnostic apparatus according to claim 10, wherein
    the modulated transmission signal which is generated by the transmission signal processing section is delayed by a delay amount in accordance with a depth of the target position, to form the reference signal.

12. The ultrasound diagnostic apparatus according to claim 10, wherein
    a modulation signal to be used for the frequency modulation processing is delayed by a delay amount in accordance with the depth of the target position to obtain a delayed modulation signal, and the carrier wave signal is subjected to the frequency modulation processing by using the delayed modulation signal.

13. The ultrasound diagnostic apparatus according to claim 10, wherein
    a modulation index of the frequency modulation processing performed by the transmission signal processing section is adjusted to set a position resolution.

14. The ultrasound diagnostic apparatus according to claim 13, wherein
    the modulation index of the frequency modulation processing performed by the transmission signal processing section is a ratio of a maximum frequency deviation and a modulation frequency and is set to a value which is 1 or greater.

15. The ultrasound diagnostic apparatus according to claim 13, wherein
    the modulation index of the frequency modulation processing performed by the transmission signal processing section is a ratio of a maximum frequency deviation and a modulation frequency and is set to a value which is 30 or greater.

16. The ultrasound diagnostic apparatus according to claim 1, wherein
    the transmission signal processing section applies a phase modulation processing to a carrier wave signal to generate the modulated transmission signal.

17. The ultrasound diagnostic apparatus according to claim 1, wherein the transmission signal processing section generates the modulated transmission signal based on data of a continuous wave having a frequency varied periodically.

* * * * *